(12) United States Patent
Charette et al.

(10) Patent No.: US 6,360,607 B1
(45) Date of Patent: Mar. 26, 2002

(54) SOUND DETECTOR DEVICE

(75) Inventors: Francois Charette, Canton; Hsiao-An Hsieh, Troy; Keng D. Hsueh, West Bloomfield; Vy Tran, Canton; Rick Hooker, Westland, all of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/369,829

(22) Filed: Aug. 9, 1999

(51) Int. Cl.[7] ................................................ G01N 29/14
(52) U.S. Cl. ........................................ 73/587; 73/584
(58) Field of Search ........................... 73/587, 584, 592, 73/116

(56) References Cited

U.S. PATENT DOCUMENTS

| 3,365,935 A | 1/1968 | Kane |
| 3,695,098 A | 10/1972 | Kirkland, Jr. |
| 4,038,866 A | 8/1977 | Johnson |
| 4,388,494 A | * 6/1983 | Schone et al. ............... 179/1 G |
| 4,649,743 A | 3/1987 | Sugimoto et al. |
| 4,739,513 A | 4/1988 | Kunugi et al. |
| 5,435,185 A | 7/1995 | Eagan |
| 5,445,026 A | 8/1995 | Eagan |
| 5,551,298 A | 9/1996 | Rayment |

FOREIGN PATENT DOCUMENTS

| DE | 3201897 | * 8/1983 | ................... 73/116 |
| JP | 189600 | * 7/1997 | |

OTHER PUBLICATIONS

Translation de 3201897.*

* cited by examiner

Primary Examiner—Hezron Williams
Assistant Examiner—Nashmiya Fayyaz
(74) Attorney, Agent, or Firm—David B. Kelley

(57) ABSTRACT

A sound detector device for locating and diagnosing sound in a motor vehicle includes a headphone and a plurality of directional microphones. The sound detector device also includes a main unit having a circuit operatively connected to the headphone and the directional microphones for allowing an operator to diagnose sound in the motor vehicle.

20 Claims, 2 Drawing Sheets

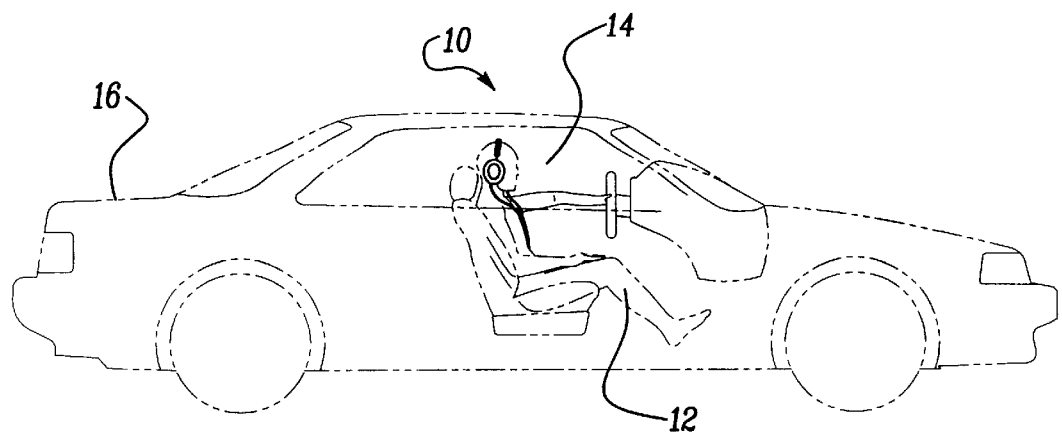
Fig-1
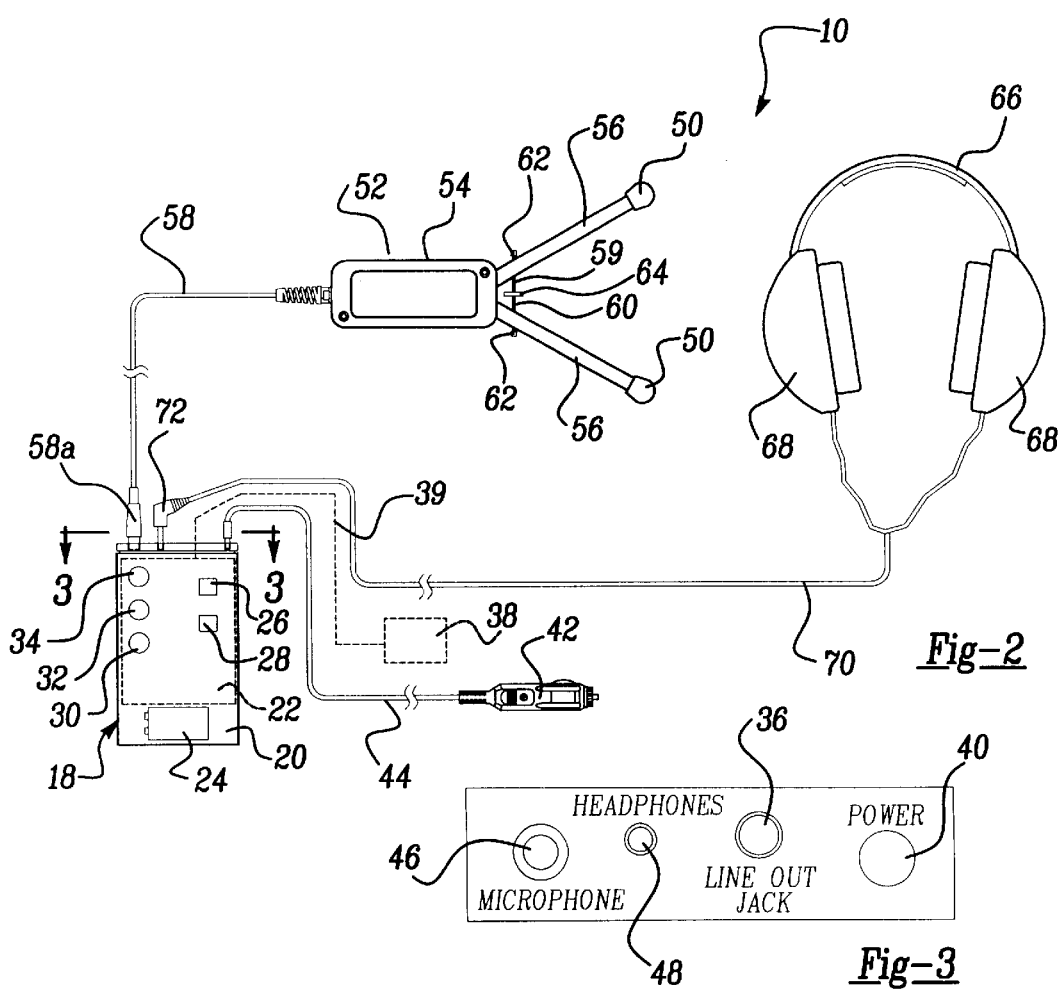
Fig-2
Fig-3

SOUND DETECTOR DEVICE

BACKGROUND OF THE INVENTION

1. Field of the Invention

The present invention relates generally to sound detecting devices for motor vehicles and, more specifically, to a sound detector device for locating and diagnosing sounds in a motor vehicle.

2. Description of the Related Art

Motor vehicle manufacturers aim to eliminate rattles, squeaks and other unexpected or undesired noises that might occur when a motor vehicle is in use. One known apparatus to locate and correct a source of the noises is disclosed in U.S. Pat. No. 5,551,298. In this patent, an apparatus is provided for identification of vibration induced noises on vehicles on a stationary test facility. Another known apparatus to locate and correct the source of noises is disclosed in U.S. Pat. No. 5,445,026. In this patent, an electronic instrument is provided for locating and diagnosing engine sounds for a motor vehicle. The electronic instrument has a single microphone connected to a hand-held electronic housing with a circuit therein and a headset connected to the housing. The electronic instrument has frequency filtering limited to "A" and "C" weighting such that only low frequencies are filtered.

Although the above apparatuses have worked to identify the source of noises in vehicles, it is desirable to provide a device for dealers and assembly plant operators to allow them to effectively diagnose squeak, rattle and unexpected noise in a vehicle and its subsystems. It is also desirable to provide a device that detects, locates and records these sounds. Therefore, there is a need in the art to provide a sound detector device for a motor vehicle.

SUMMARY OF THE INVENTION

Accordingly, the present invention is a sound detector device for locating and diagnosing sound in a motor vehicle including a headphone and a plurality of directional microphones. The sound detector device also includes a main unit having a circuit operatively connected to the headphone and the directional microphones for allowing an operator to diagnose sound in the motor vehicle.

One advantage of the present invention is that a sound detector device is provided for a motor vehicle. Another advantage of the present invention is that the sound detector device allows an operator to diagnose sounds such as a squeak, rattle and unexpected noise in a motor vehicle and its subsystems. Yet another advantage of the present invention is that the sound detector device has two directional microphones to enhance the localization of the source of the sounds. Still another advantage of the present invention is that the sound detector device has adjustable band pass filtering that allows the user to select the center frequency and bandwidth. A further advantage of the present invention is that the sound detector device is hand-held. Still a further advantage of the present invention is that the sound detector device is relatively low cost.

Other features and advantages of the present invention will be readily appreciated, as the same becomes better understood after reading the subsequent description taken in conjunction with the accompanying drawings.

BRIEF DESCRIPTION OF THE DRAWINGS

FIG. 1 is an elevational view of a sound detector device, according to the present invention, illustrated in operational relationship with an operator and a motor vehicle.

FIG. 2 is a plan view of the sound detector device of FIG. 1.

FIG. 3 is a view taken along line 3—3 of FIG. 2.

DESCRIPTION OF THE PREFERRED EMBODIMENT(S)

Figure 4:
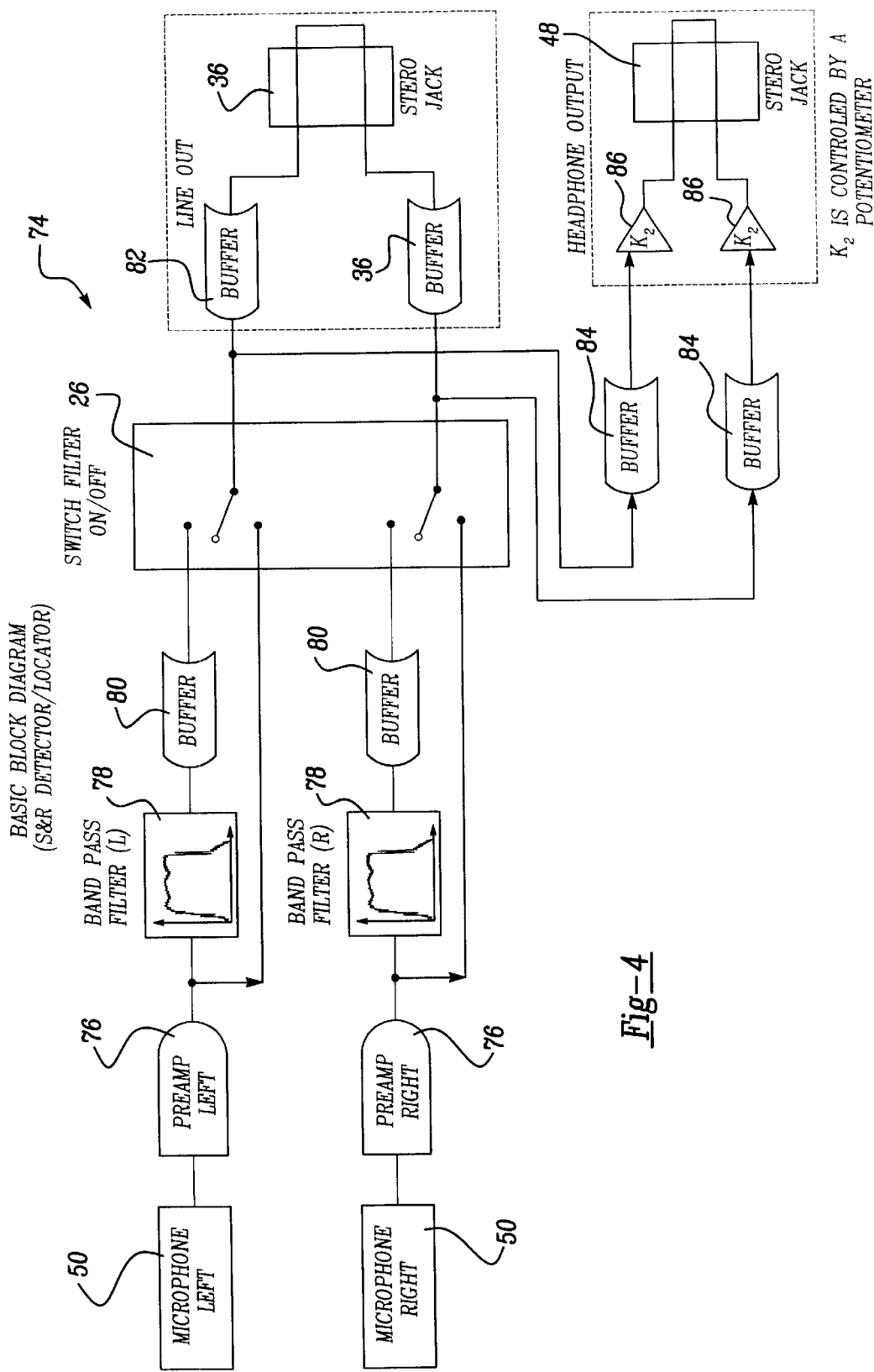
FIG. 4 is a block diagram of the sound detector device of FIG. 1.

Referring to the drawings and in particular FIGS. 1 and 2, one embodiment of a sound detector device 10, according to the present invention, is illustrated for an operator 12 located in an occupant compartment 14 of a motor vehicle 16. The sound detector device 10 is to be used by the operator 12 to detect, locate and record sounds such as squeaks, rattles and unexpected noises in the motor vehicle 16.

Referring to FIGS. 2 and 3, the sound detector device 10 includes an electronic main unit, generally indicated at 18. The main unit 18 includes a housing 20 conformed to be held in the hand of the operator 12. In the embodiment illustrated, the housing 20 is generally rectangular in shape. The main unit 18 includes a circuit board 22 having a circuit to be described disposed within an interior of the housing 20. The main unit 18 also includes a power source 24 such as a battery disposed in the interior of the housing 20 and electrically connected to the circuit board 22 by suitable means such as wires (not shown). The power source 24 is preferably a nine-volt (9V) battery. The main unit 18 includes an ON/OFF switch 26 electrically connected to the circuit board 22 by suitable means such as wires (not shown) for a function to be described. The main unit 18 also includes a MONO/STEREO switch 28 electrically connected to the circuit board 22 by suitable means such as wires (not shown) that allows the operator 12 to monitor one or more microphones to be described. The main unit 18 includes a volume control knob 30 to adjust or control a volume output of the main unit 18. The main unit 18 includes a frequency control button 32 to adjust or control the frequency of a filter for the circuit to be described. The main unit 18 also includes a bandwidth control button 34 to adjust or control the bandwidth of a filter for the circuit to be described. The main unit 18 further includes a line out jack 36 electrically connected to the circuit board 22 by suitable means such as wires (not shown) to output a signal to a recorder 38 by suitable means such as a cable 39. The main unit 18 includes a power input jack 40 electrically connected to the circuit board 22 by suitable means such as wires (not shown). The power input jack 40 allows power to be inputted to the circuit by a power plug 42 via a cable 44 to a lighter (not shown) of the motor vehicle 16. The main unit 18 also includes a microphone jack 46 electrically connected to the circuit board 22 by suitable means such as wires (not shown) to allow a signal of sounds detected to be inputted via microphones to be described. The main unit 18 further includes a headphone jack 48 electrically connected to the circuit board 22 by suitable means such as wires (not shown) to allow an output signal to a headphone to be described.

Referring to FIGS. 1 and 2, the sound detector device 10 also includes a plurality of, preferably two microphones 50 for detecting and converting audible acoustic signals and sounds into electromagnetic signals. The sound detector device 10 includes a separation distance mechanism, generally indicated at 52, for supporting and directionally moving the microphones 50. The separation distance mechanism 52 includes a housing 54 having a pair of arms 56 extending outwardly therefrom. The arms 56 are pivotally connected to the housing 54 by suitable means (not shown).

The microphones 50 are mounted to the arms 56 and are electrically connected by suitable means such as wires (not shown) extending through the housing 54 to a cable 58 extending into the interior thereof. The cable has a plug 58a for electrical connection to the microphone jack 46 of the main unit 18.

The separation distance mechanism 52 also has an adjustment mechanism 59 such as a threaded rod 60 extending transversely through the threaded apertures (not shown) in the arms 56 to adjust the distance between the arms 56. The adjustment mechanism 59 includes a nut 62 on each end of the threaded rod 60 and a distance wheel 64 located between the arms 56 such that the operator 12 can rotate the distance wheel 64, in turn, rotating the threaded rod 60 and moving the arms 56 toward and away each other. The separation distance between the microphones 50 is approximately 0.5 inches to approximately 5.75 inches to tune and zoom in a location of the source of the sounds. It should be appreciated that the nuts 62 act as a stop for a maximum adjustment of the arms 56 away from each other.

The sound detector device 10 further includes a headphone 66 to allow the operator 12 to listen to the sound through the microphones 50. The headphone 66 includes earphones 68 for electrical connection via a cable 70 with a plug 72 to the headphone jack 48 of the main unit 18. It should be appreciated that the headphone 66 is conventional and known in the art. It should also be appreciated that the headphone 66 and line out jack 36 allows for simultaneous listening and recording.

Referring to FIG. 4, the sound detector device includes a circuit, generally indicated at 74 and according to the present invention, for the circuit board 22. The circuit 74 includes the microphones 50, which are a left and right microphone, and a pre-amplifier 76 electrically connected to each one of the microphones 50 to amplify the signals from the microphones 50. The circuit 74 also includes an adjustable band pass filter 78 electrically connected to each one of the pre-amplifiers 76 to filter the amplified signals and mechanically connected to the frequency control button 32 and bandwidth control button 34. The buttons 32 and 34 control band pass filtering by selecting a center frequency and frequency bandwidth for the sounds through the microphones 50. The circuit 74 includes a buffer 80 electrically connected to each of the band pass filters 78 to buffer the filtered signals. The circuit 74 includes the ON/OFF switch 26 for the band pass filters 78. In the ON position, the amplified signal is filtered via the band pass filters 78. In the OFF position, the amplified signal is not filtered by the band pass filters 78. The circuit 74 includes a pair of buffers 82 electrically connected to the ON/OFF switch 26 and the line out jack 36 electrically connected to the buffers 82. The circuit 74 includes another pair of buffers 84 electrically connected to the ON/OFF switch 26 and at least one volume control (K2) potentiometer 86 electrically connected to the buffers 84 and mechanically connected to the volume control knob 30. The circuit 74 includes the headphone jack 48 electrically connected to the volume control potentiometer 86. It should be appreciated that the circuit 72 may include other components (not shown) for operation thereof.

In operation of the sound detector device 10, power flows from either the power source 24 or the plug 42 and cable 44 to the circuit 74. The recorder 38 may be connected to the main unit 18 via the cable 39 to record sound through the microphones 50. The operator 12 places the headphone 66 over their head and the earphones 66 over their ears to listen for sound through the microphones 50. The operator 12 can adjust the volume of the sounds to their ears via the volume control knob 30. The operator 12 can adjust the frequency and bandwidth of the sounds through the microphones 50 via the control buttons 32 and 34 and change the separation distance between the two directional microphones 50 via the distance separation mechanism 52 to enhance the listening of the desired sound. Once the operator 12 has focus on the squeak, rattle or unexpected noise, he/she can much more efficiently find the root cause or record the sound using the line out jack 36, cable 39 and recorder 38 for further analysis.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A sound detector device for locating and diagnosing sound in a motor vehicle comprising:
   a headphone;
   a plurality of directional microphones being directionally movable by a distance separation mechanism; and
   a main unit having a circuit operatively connected to said headphone and said directional microphones for allowing an operator to diagnose sound in the motor vehicle.

2. A sound detector device as set forth in claim 1 including a recorder electrically connected to said circuit for recording signals therefrom.

3. A sound detector device as set forth in claim 1 wherein said distance separation mechanism interconnects said directional microphones and said circuit.

4. A sound detector device for locating and diagnosing sound in a motor vehicle comprising:
   a headphone;
   a plurality of directional microphones;
   a main unit having a circuit operatively connected to said headphone and said directional microphones for allowing an operator to diagnose sound in the motor vehicle;
   a distance separation mechanism interconnecting said directional microphones and said circuit; and
   wherein said distance separation mechanism comprises a housing having a plurality of movable arms extending outwardly therefrom, one of said directional microphones being attached to one of said movable arms.

5. A sound detector device as set forth in claim 4 wherein said distance separation mechanism includes an adjustment mechanism connected to said movable arms to move said movable arms toward and away from each other to change a separation distance therebetween.

6. A sound detector device as set forth in claim 1 wherein said main unit comprises a housing, a circuit board having said circuit disposed in said housing and a power source disposed in said housing and electrically connected to said circuit.

7. A sound detector device as set forth in claim 1 including a power plug electrically connected to said circuit for attachment to a power source of the motor vehicle.

8. A sound detector device as set forth in claim 1 wherein said circuit includes a plurality of bandpass filters electrically connected to said directional microphones for filtering a signal from said directional microphones.

9. A sound detector device as set forth in claim 8 wherein said main unit includes a control button for adjusting a frequency of said bandpass filters.

10. A sound detector device as set forth in claim 8 wherein said main unit includes a control button for adjusting a band width of said bandpass filters.

11. A sound detector device as set forth in claim 8 wherein circuit includes an ON/OFF switch electrically connected to said bandpass filters and said directional microphones for turning said bandpass filters ON to filter the signals from said directional microphones and for turning said bandpass filters OFF to allow the signals from said directional microphones to bypass said bandpass filters.

12. A sound detector device as set forth in claim 11 wherein said circuit includes a plurality of pre-amplifiers electrically interconnecting said directional microphones and said bandpass filters and said ON/OFF switch.

13. A sound detector device as set forth in claim 11 wherein said circuit includes a plurality of buffers interconnecting said bandpass filters and said ON/OFF switch.

14. A sound detector device as set forth in claim 11 wherein said circuit includes at least one buffer electrically connected to said ON/OFF switch, a volume potentiometer electrically connected to said at least one buffer and a headphone jack electrically connected to said volume potentiometer.

15. A sound detector device as set forth in claim 11 wherein said circuit includes at least one buffer electrically connected to said ON/OFF switch and a line out jack electrically connected to said at least one buffer.

16. A sound detector device for locating and diagnosing sound in a motor vehicle comprising:

a headphone;

a plurality of directional microphones being directionally movable by a distance separation mechanism; and a main unit having a circuit operatively connected to said headphone and said directional microphones for allowing an operator to diagnose sound in a motor vehicle;

said circuit comprising a plurality of pre-amplifiers electrically connected to said directional microphones for amplifying signals from said directional microphones, a plurality of bandpass filters electrically connected to said pre-amplifiers for filtering a signal from said pre-amplifiers, and an ON/OFF switch electrically connected to said bandpass filters and said directional microphones for turning said bandpass filters ON to filter the signals from said directional microphones and for turning said bandpass filters OFF to allow the signals from said directional microphones to bypass said bandpass filters; and means for adjusting at least one of a frequency and bandwidth of said bandpass filters.

17. A sound detector device as set forth in claim 16 wherein said circuit includes a plurality of buffers interconnecting said bandpass filters and said ON/OFF switch.

18. A sound detector device as set forth in claim 16 wherein said circuit includes at least one buffer electrically connected to said ON/OFF switch, a volume potentiometer electrically connected to said at least one buffer and a headphone jack electrically connected to said volume potentiometer.

19. A sound detector device as set forth in claim 16 wherein said circuit includes at least one buffer electrically connected to said ON/OFF switch and a line out jack electrically connected to said at least one buffer.

20. A sound detector device for locating and diagnosing sound in a motor vehicle comprising:

a headphone;

a plurality of directional microphones;

a main unit having a circuit operatively connected to said headphone and said directional microphones for allowing an operator to diagnose sound in the motor vehicle;

a distance separation mechanism interconnecting said directional microphones and said circuit, said distance separation mechanism having a plurality of movable arms extending outwardly therefrom, one of said directional microphones being attached to one of said movable arms, and an adjustment mechanism connected to said movable arms to move said movable arms toward and away from each other; and a recorder electrically connected to said circuit for recording signals therefrom.

\* \* \* \* \*